United States Patent [19]

Nelson

[11] Patent Number: 4,960,135

[45] Date of Patent: Oct. 2, 1990

[54] ANKLE RESTRAINT DEVICE

[76] Inventor: Ronald E. Nelson, 405 Sunset La., Cambridge, Minn. 55008

[21] Appl. No.: 298,697

[22] Filed: Jan. 19, 1989

[51] Int. Cl.⁵ ............................................. A61F 5/00
[52] U.S. Cl. ................................. 128/80 H; 128/166
[58] Field of Search ............................ 128/80 H, 166

[56] References Cited

U.S. PATENT DOCUMENTS

| 28,897 | 6/1911 | Ward | 128/166 |
|---|---|---|---|
| 325,280 | 9/1885 | Smadbeck et al. | |
| 470,316 | 3/1892 | Brown | 128/80 H |
| 938,440 | 10/1909 | Sescila | 128/166 |
| 2,096,677 | 10/1937 | Fassett | |
| 2,774,152 | 12/1956 | Alber | 128/166 |
| 2,994,322 | 8/1961 | Cullen et al. | |
| 3,674,023 | 7/1972 | Mann | 128/166 |
| 3,970,083 | 7/1976 | Carrigan | |
| 4,237,874 | 12/1980 | Nelson | 128/166 |
| 4,280,488 | 7/1981 | Polsky et al. | 128/166 |
| 4,323,058 | 4/1982 | Detty | 128/80 H |
| 4,527,556 | 7/1985 | Nelson | 128/166 |
| 4,621,648 | 11/1986 | Ivany | 128/80 H |
| 4,724,847 | 2/1988 | Nelson | 128/80 H |
| 4,753,229 | 6/1988 | Sutherland | 128/80 H |
| 4,869,267 | 9/1989 | Grim et al. | 128/80 H |

Primary Examiner—Edgar S. Burr
Assistant Examiner—Huong Q. Pham
Attorney, Agent, or Firm—Burd, Bartz & Gutenkauf

[57] ABSTRACT

An ankle restraint device having a first or outer ankle brace configured to substantially conform to the lower leg, ankle and foot of the wearer and offer generalized support. A second or inner brace is imbedded between first and second side walls of the outer brace and is specifically configured to encompass the heel and bind it to the remainer of the foot in a heel lock type configuration. The inner brace acts independently of the outer brace and has forward edge portions with arms that extend through openings on the outer brace for purposes of fastening the forward edges of the inner brace together in order to bind the heel. Both the inner brace and outer brace have fastening means which can include a single shoelace trained through eyelets formed in forward edges of the inner brace and outer brace. In one form of the invention, the brace assembly is installed with respect to an outer item of footwear apparel such as an athletic shoe.

18 Claims, 3 Drawing Sheets

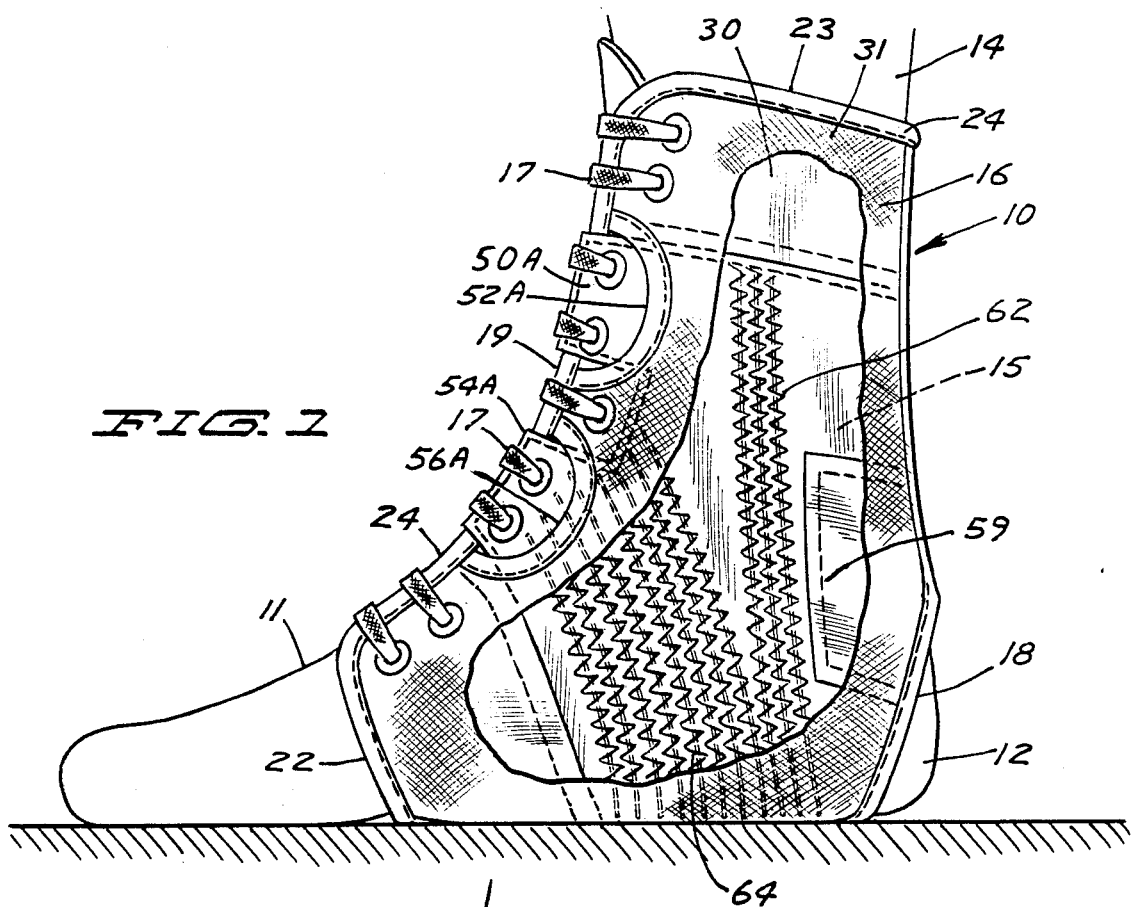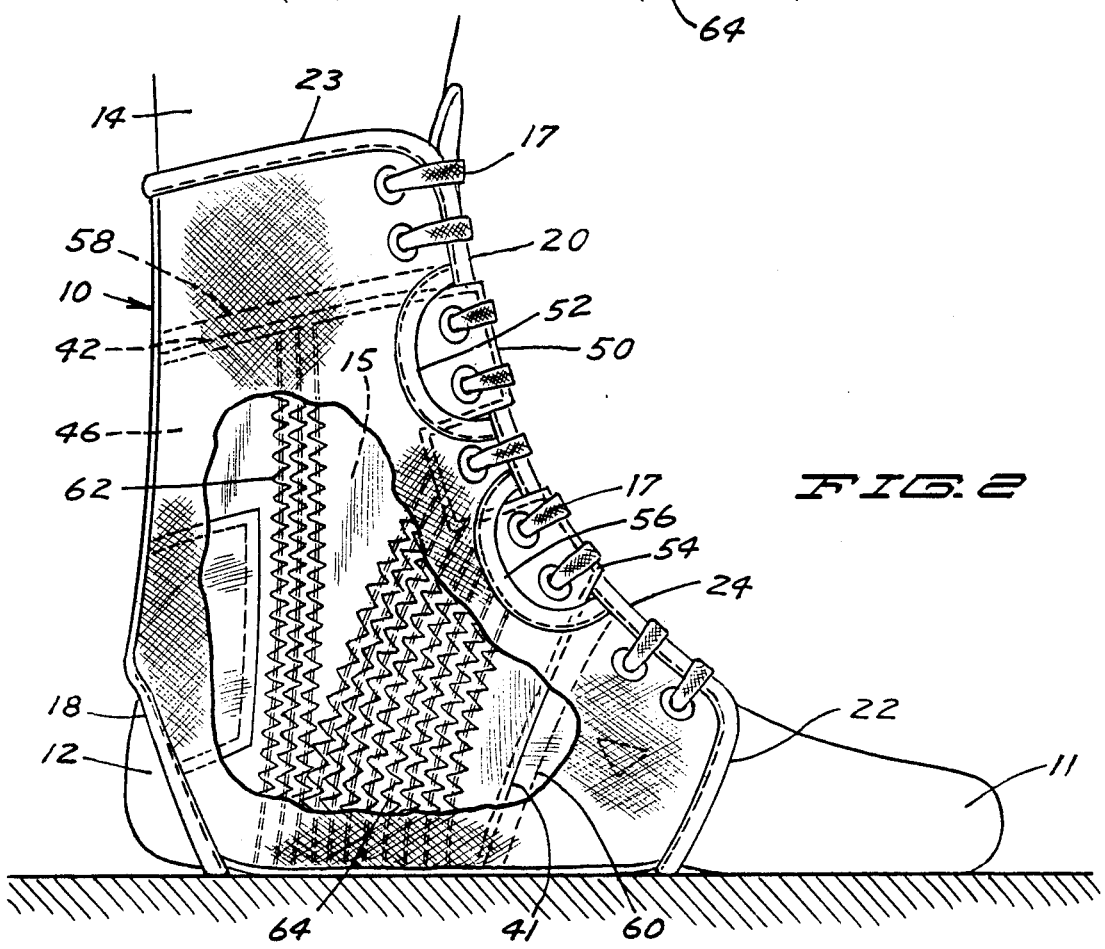

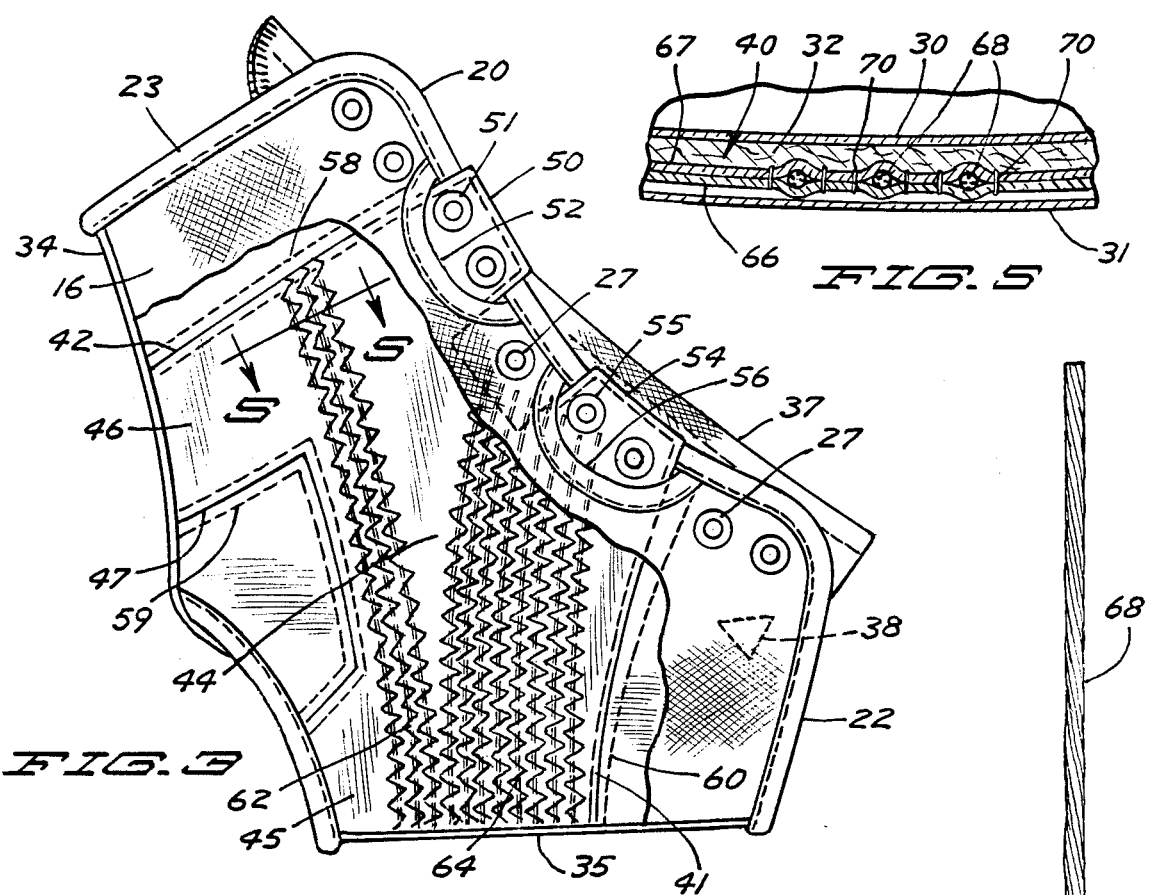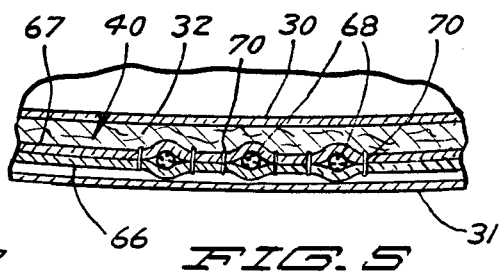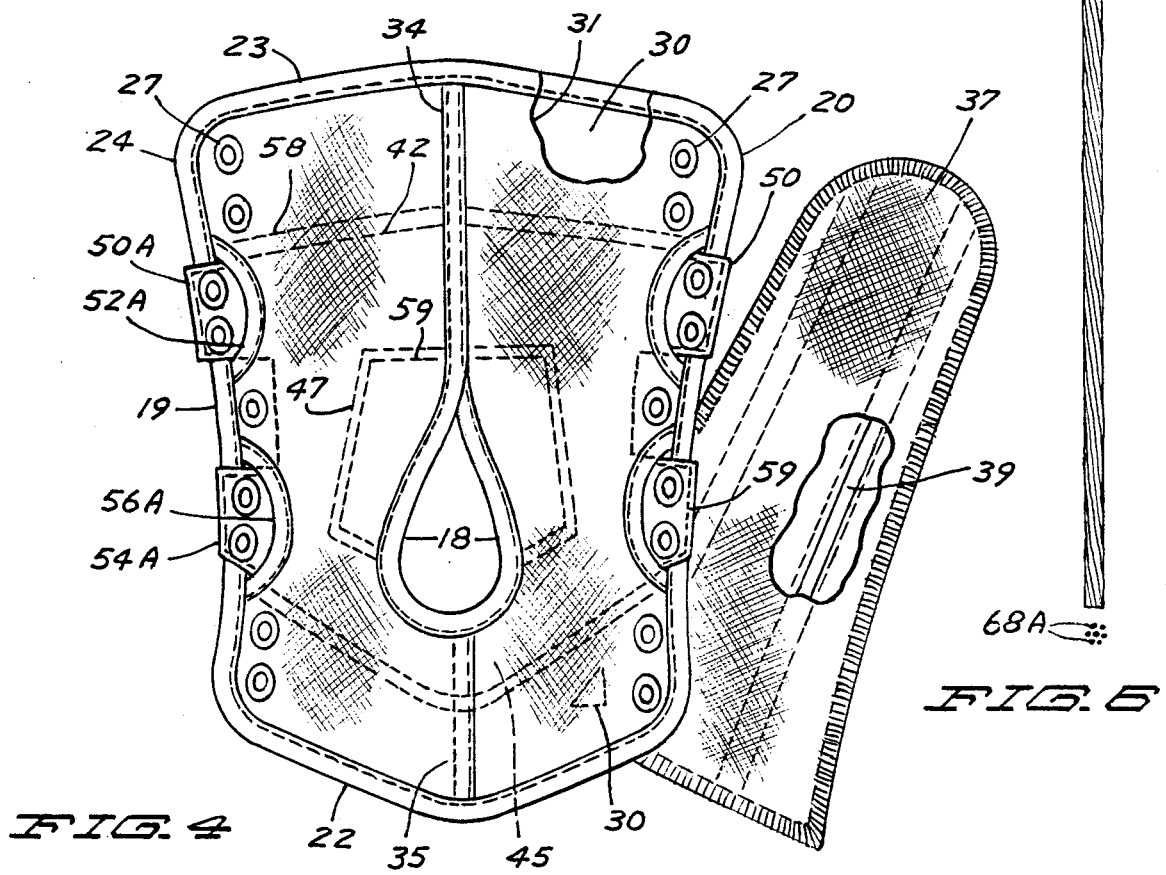

ANKLE RESTRAINT DEVICE

BACKGROUND OF THE INVENTION

Athletes commonly wear ankle and foot braces to bind together the separate bones of the foot, ankle and lower leg in a neutral position so that traumatic experiences otherwise tending to separate the bones of the joints and damage the connecting ligaments will result in restrained movement hopefully not much beyond the normal limits of flexure, extension and twisting so as to avoid damage to the ligaments or other injury. Constraining relative movement of the bones at the joints, both the ankle joint and the talo-calcaneo joint which lies just below the true ankle joint, is also important during the healing of an injured ligament or an injury to the bone structure itself. The ankle joint is meant to move in only one direction, flexure and extension or flexing and extending the foot up and down. Side to side movement of the foot and normal twisting motion occurs in the talo-calcaneo joint.

In order to place the foot, ankle and lower leg in a condition of constraint when in a neutral position, athletes employ various tape configurations involving a technique known as a heel lock where the heel is significantly restrained from movement relative to the ankle and the remainder of the foot. An example of a particular technique is that known as a closed basketweave with heel locks. This involves applying an underwrap directly to the skin, then applying anchor straps at the mid-foot and at the lower leg. This is followed by alternately applying vertical stirrups of tape extending from the lateral to the medial sides of the leg and under the foot, and horizontal strips of tape extending from the front superior foot surface, around the back of the foot and then back to the front superior foot surface. Strips of tape are then applied starting at the top of the foot, under the bottom of the foot at a 45 degree angle, to a location behind the heel and then around the ankle, on both the lateral and medial sides. The foot constraint acheived is good but a large amount of tape is consumed as well as time in installing and removing such a tape wrap.

SUMMARY OF THE INVENTION

The invention pertains to a foot and ankle restraint or brace assembly for generalized support of the foot and ankle region and for more specific support to the heel and foot in creating a heel lock type of brace to relatively immobilize the heel relative to the foot and ankle. This substantially restrains the foot and ankle in a normal position when engaged in rigorous activity so as to eliminate or substantially decrease the likelihood of a foot or ankle injury due to hyperextension of the foot and ankle beyond normal limitations.

The ankle restraint includes an outer brace formed of a sheet-like base of inner and outer layers or side walls shaped to closely conform to the foot and ankle of the wearer to provide generalized support to the ankle region. A second or inner brace is installed between the inner and outer side walls of the outer brace and is specifically contoured to wrap around the heel and the sole of the foot and the front superior foot portion independently of the outer brace. The inner brace provides support independent of the outer brace to the heel and ankle and front of the foot in order to substantially immobilize the heel with respect to the ankle and foot. In one preferred embodiment of the invention the ankle restraint device includes an inner brace and an outer brace both installed in and forming an intregal part of an item of outer foot apparel such as a high top shoe or boot.

IN THE DRAWINGS

FIG. 1 is a side elevational view of one side of an ankle restraint device according to the invention installed on a foot with a portion broken away for purposes of illustration;

FIG. 2 is a side elevational view of the other side of the ankle restraint device shown in FIG. 1 with a portion broken away for illustration;

FIG. 3 is a side elevational view of the ankle restraint device of FIG. 2 shown removed from the foot and partially fragmented for illustration;

FIG. 4 is a rear elevational view of the ankle restraint device of FIG. 3 in a spread open configuration for purposes of illustration;

FIG. 5 is an enlarged sectional view of a portion of the ankle restraint device of FIG. 3 taken along the line 5—5 thereof;

FIG. 6 is an enlarged side elevation and end view of one of the metal strands shown in FIG. 5;

DESCRIPTION OF PREFERRED EMBODIMENTS

Figure 7:
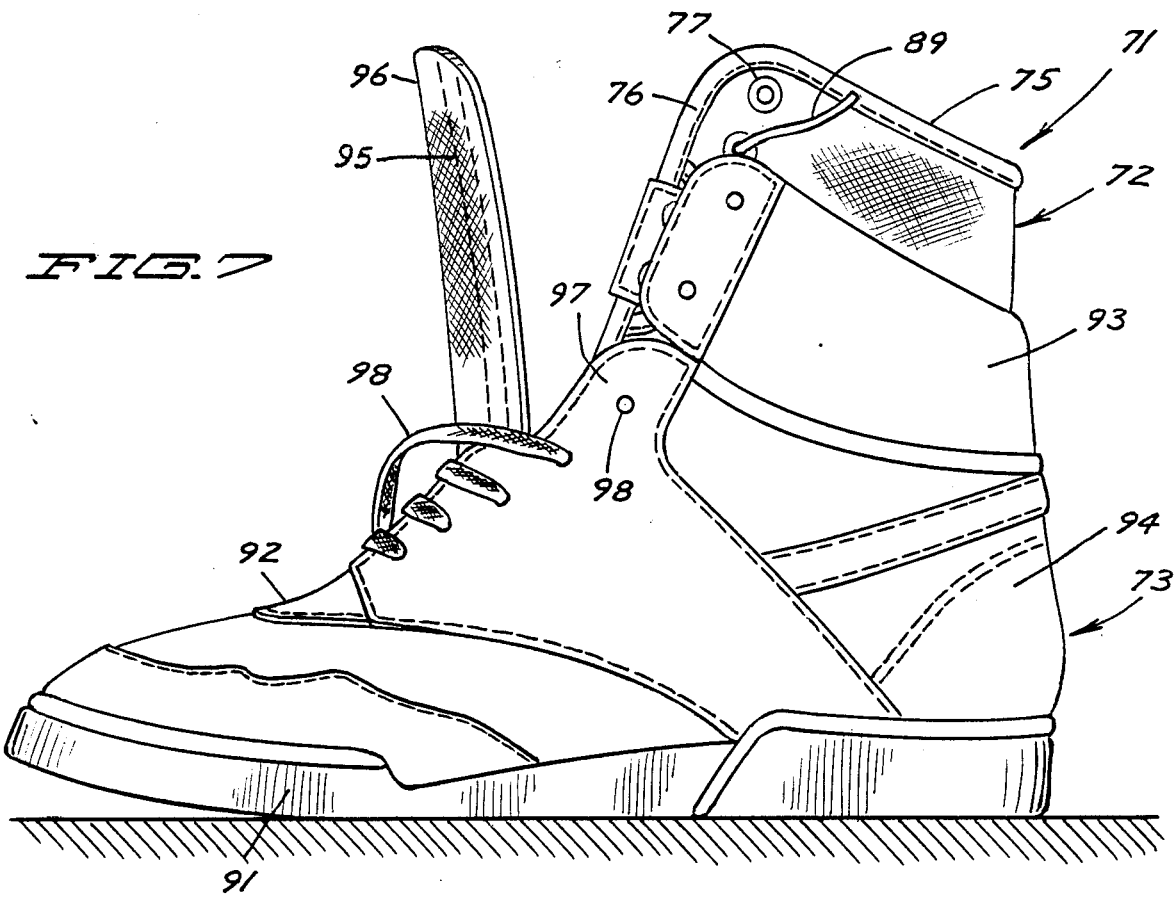
FIG. 7 is a side elevational view of an ankle restraint device which includes an item of outer footwear apparel.

Referring to the drawings, there shown in FIGS. 1 and 2 an ankle restraint device according to one form of the invention indicated generally at 10 installed on the lateral and medial sides respectively of a foot 11 encompassing the heel 12 of foot 11 and the intervening ankle region 15 between the foot and the lower leg 14. The ankle joint is the joint between the leg and the foot in which the tibia and the fibula above articulate with the talus below. The ankle is the region of the joint. The various bones comprising the ankle joint are interconnected by ligaments which are susceptible to damage upon hyperextension or movement of the bones apart from one another beyond normal limitation, and upon undo twisting or abnormal movement of the bones with respect to one another. An effective way to restrain such movement is known as a heel lock technique whereby the heel is bound to the remainder of the foot and ankle when in the normal position so that it is restrained from undo extension beyond that position whereby the various ligaments attaching the heel to the remainder of the foot, such as the anterior talofibular ligament are not stretched beyond normal limitations. The ankle restraint device 10 is effective to provide such a heel lock to the foot 11 and heel 12 to compress them in the ankle region toward one another when in a relaxed state. Upon engagement in rigorous activity and extension of the ankle joint, the bones move first through a normal position and then to a normal extended position. The joints are inhibited from entering a hyperextended condition or from undo twisting movement.

Ankle restraint device 10 includes a first or outer brace to provide generalized support to the foot and ankle region, and a second or inner brace to specifically provide a heel lock type support between the heel 12 and foot 11 and ankle region 15. A flexible composite jacket or base 16 comprises the outer brace and is shaped to be wrapped in conforming relationship around lateral and medial sides of the foot and ankle. The outer brace 16 has a top edge 23 that wraps around the lower leg 14 with ends coming toward one another forming a top or leg opening when installed on a foot. A bottom edge 22 wraps around the mid-foot area and has ends coming toward each other to form a front or foot opening. Forward edges 19, 20 that extend between the ends of the top and bottom edges come toward one another over the front superior foot surface for fastening by suitable means such as a common lace 17. A continuous edge binding 24 is sewn to the various edges. The forward edges 19, 20 carry lace openings reinforced by eyelets 27. Lace 17 is trained through the eyelets 27 to bring and hold together the forward edges 19, 20 in place relative to one another and to bind the outer brace on the foot.

Outer brace 16 includes an inner layer or side wall 30 and an outer layer or side wall 31 fixed to inner side wall 30 by the edge stitching associated with the binding 24 (see FIG. 4). Side walls 30, 31 are formed of a strong, flexible and relatively inelastic material such as canvass or vinyl. Both side walls are formed of relatively symmetrical half sections that are sewn together by a seam that becomes a rear vertical seam 34 extending along the back of the foot, and a short horizontal seam 35 that extends along the foot sole when the brace is installed on a foot. The heel opening 18 separates the horizontal seam 35 and the vertical seam 34.

A tongue 37 is fixed to the inside of outer brace 16 approximate the lower end of one of the forward edges by suitable stiching 38. Tongue 37 is adapted for covering the usual forward superior foot, ankle and lower leg portion between the forward edges 19, 20 in usual fashion. As shown in FIG. 4, tongue 37 has a pair of elongate stiffening members 39 extending substantially the length thereof.

Ankle restraint 10 has an inner or second brace 40 imbedded between the inner and outer side walls 30, 31 of outer brace 16 and situated to independently give support to the heel and foot along with the outer brace 16. Inner brace 40 is somewhat smaller than the outer brace 16 and is specifically shaped and positioned to encompass the heel of the foot and bind it to the front superior foot portion and the ankle.

Inner brace 40 has lateral and medial sides connected to each other and to the outer brace 16 at the rear vertical seam 34 and the bottom horizontal seam 35. In FIG. 3 the intermediate portion of the medial side of the outer brace 16 is broken away for purposes of illustration to expose the medial side of the inner brace 40. The lateral and medial sides of the inner brace 40 are symmetrical whereby a discription of the medial side applies also to the lateral side. A bottom edge 41 wraps around the foot from the transverse arch to the upper foot surface. A top edge 42 wraps around the lower leg just above the ankle and beneath the top edge 23 of the outer brace 16. The bottom and top edges 41, 42 are spaced inwardly of the corresponding top and bottom edges 23, 22 of the outer brace 16 and are installed between the inner and outer layers 30, 31 of the outer brace 16. A central portion or side wall 44 of the medial side of the inner brace 40 covers the medial malleous of the ankle and surrounding areas. Central portion 44 extends downwardly to a lower strap 45 that extends under the arch of the foot to the lower horizontal seam 35 and also rearwardly to the heel opening 18. The upper end of the central portion 44 has a rearwardly extended strap 46 that extends to the rear vertical seam 34. A cut out portion or opening 47 is located between the lower strap 45 and the upper strap 46. When the central portion 44 is placed in tension, the lower strap 45 tends to lift or bind the lower portion of the heel, while the upper strap 46 binds the upper extremity of the heel.

An upper medial arm 50 extends forward from the upper portion of the medial side of inner brace 40 opposite the upper strap 46. The arm 50 carries a pair of eyelets 51. The arm 50 extends through a side wall opening 52 formed between the inner and outer side walls 30, 31 of the outer brace 16 such that the eyelets 51 are generally aligned with the lace eyelets 27 of the outer brace 16. A lower medial arm 54 extends from the central portion 44 of the medial side of the inner brace 40 toward the forward edge 20 of the outer brace 16. The lower arm 54 carries a pair of lace eyelets 55. The arm 54 extends through a lower side wall opening 56 formed between the inner side wall 30 and outer side wall 31 of the outer brace 16. The arm 54 is positioned such that the eyelets 55 are also generally in alignment with the eyelets 27 on the forward edge 20 of the outer brace 16 for receipt of a common lace. As shown in FIGS. 1 and 4, symmetrical arms 50A, 54A external through openings 52A, 56A on the opposite side of ankle restraint 10.

The outer brace 16 has an upper stitch 58 which forms a top boundary for the inner brace 40. An intermediate stitch 59 on outer brace 16 is formed parallel to the edges of the opening 47 between the inner and outer side walls 30, 31. A forward stitch 60 is formed between the inner and outer side walls 30, 31 of the outer brace 16 and is located just forward of the bottom edge 41 of the inner brace 40. The medial side of inner brace 40 is loose between the inner and outer side walls 30, 31 of the outer brace 16, and is fastened only at the bottom seam 35 and the rear vertical seam 34. The upper stitch 58, intermediate stitch 59 and forward stitch 60 form boundries for the inner brace 40.

Each side of the inner brace 40 has two sets of tension members embedded therein in order to concentrate the tension forces placed on the brace to more effectively bind the heel. A first set 62 of tension members extends from the arch of the brace upwardly along the side thereof to the upper edge 42 passing over the malleous. A second set 64 of tension members begins at the arch of the foot and extends upwardly and curves slightly forward over the front superior foot surface to the forward edge of the brace proximate the eyelets. A preferred form of tension member is shown in FIG. 5. The wall of a portion of the inner brace 40 is shown to be comprised of adjacent first and second layers or plies 66, 67 of flexible, sheet-like material such as vinyl or canvas disposed closely adjacent between the layers 30,31 of the outer brace 16. Inner layer 30 can have a foam backing or pad 32. Linear flexible tension members 68 are embedded between the first and second layers 66, 67 of the side wall of inner brace 40 and are held there by a plurality of seams 70. Seams 70 can form a zig-zag pattern as shown in FIG. 1. As shown in FIG. 6, a tension member 68 is comprised of a plurality of interwoven wire elements 68A to form a unified relatively strong composite member.

In use of ankle restraint 10, the foot is positioned inside the inner layer of the outer brace 16 as shown in FIGS. 1 and 2. A shoe lace 17 is trained through the eyelets 27 on the outer brace 16 as well as the eyelets 51, 55 on the inner brace. Lace 17 can pass consecutively through the eyelets as they occur in alignment along the foot. The tongue 37 is placed over the front superior foot surface. Stiffening members 39 in tongue 37 bear against and support the front superior foot surface. When the lace 17 is tightened, the inner brace 40 is placed in tension to provide a heel lock. The lower strap 45 binds the lower extremity of the heel, and the upper strap 46 binds the upper extremity of the heel upon tightening of the arms 50, 54 across the front superior foot surface. The sets 62, 64 of tension members provide support to the ankle region.

Figure 8:
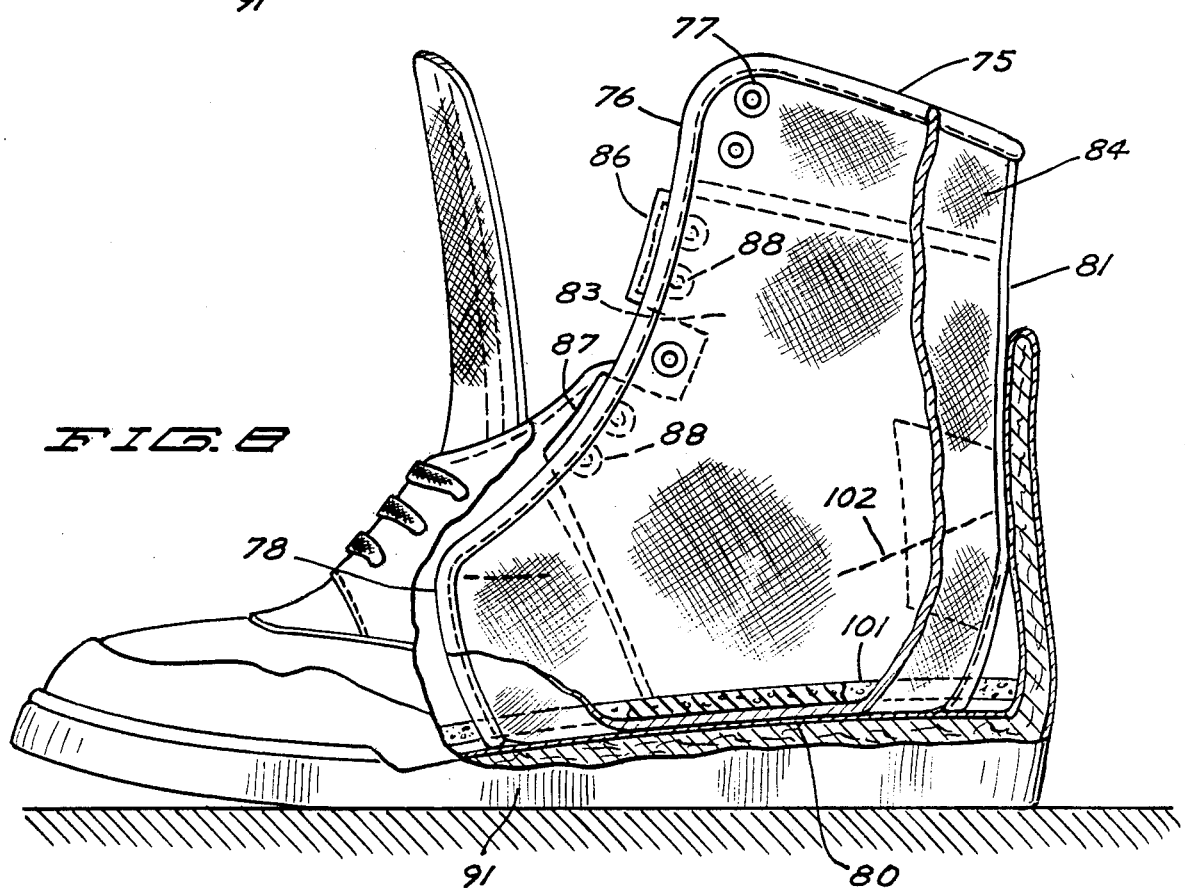
FIG. 8 is a side elevational view like that of FIG. 7 but with portions removed for purposes of illustration.

A further form of the invention is shown in FIGS. 7 and 8 wherein an ankle restraint according to the invention includes an integral outer item of foot apparel such as a high top athletic shoe. An ankle restraint indicated generally at 71 includes a brace assembly 72 assembled to an athletic shoe 73. Ankle brace assembly 72 can be like the ankle restraint device 10 described with respect to FIGS. 1-6 with the ommission of the tongue. The brace assembly 72 includes a top edge 75 that wraps around the lower leg, and front edges 76 that come together over the front superior foot surface and the forward portion of the lower leg. The front edges 76 carry eyelets 77 for receipt of a shoelace. A bottom edge 78 wraps around the mid-foot portion at the lower end of the front edges 76. A sole 80 extends beneath the arch of the foot, and a rear vertical seam 81 extends up the back of the foot and leg from the heel opening. An inner brace 83 is embedded between inner and outer layers of an outer brace 84 which comprise the brace assembly 72. The inner brace 83 has upper and lower medial and lateral arms 86, 87 which extend through openings provided at the front edges 76 of the outer brace 84 and carry eyelets 88 for use as previously discribed.

The shoe 73 has an outer sole 91 and a shoe upper including a vamp 92, top 93 and heel area 94. Forward edges 97 come together and cooperate with a tongue 96 to cover the front portion of the foot. Tongue 96 has stiffening elements 95. The forward edges have eyelets 98 that carry a standard shoelace 99 for tightening the shoe on the foot.

Brace assembly 72 is installed in the interior of shoe 73 with the bottom of the brace resting on the top of the sole of the shoe. An insole 101 can be installed inside the brace assembly for foot comfort. The brace assembly 72 is fastened to the shoe 73 by suitable means preferably approximately one quarter of the height upwards on the brace assembly 72. For example, as shown in FIG. 8 a seam 102 can be formed between the sidewall of the outer brace 84 and the shoe 73. Alternatively, a gluing process could be used.

In the use of the ankle restraint 71, the foot is installed inside of the brace assembly 72 which is then laced up through the use of laces 89. This places tension both in the inner brace 83 and the outer brace 84. The inner brace 83 provides a heel lock for the foot, while the outer brace 84 provides generalized support to the heel, ankle and foot. The wearer then laces up the lace 99 of the shoe portion 73 in the usual fashion to additionally achieve the support and protection normally provided through use of a proper atheletic shoe.

While there has been shown and described certain perferred embodiments of an ankle restraint device according to the invention, it will be apparent that certain deviations can be had from the embodiments shown without departing from the scope and spirit of the invention.

The embodiments of the invention in which an exclusive property or privilege is claimed are defined as follows:

1. An ankle restraint device to be worn on the lower leg, ankle and foot, comprising:

an outer brace formed of flexible sheet-like material configured to conform to the lower leg, ankle and mid-foot, said outer brace having a top edge that wraps around the lower leg, said top edge having ends that come toward one another forming a leg opening to the outer brace, a bottom edge that wraps around the mid-foot area, said bottom edge having ends that come toward one another on the upper foot surface to form a foot opening, and first and second forward edges extending between the ends of the top edge and the bottom edge adapted to extend toward one another around the front superior foot surface, and means for fastening the first and second forward edges with respect to one another to place the outer brace in tension around the lower leg, ankle and mid-foot, said outer brace being comprised of inner and outer layers of flexible sheet-like material joined together at said top, bottom and forward edges forming inner and outer side walls disposed in substantially co-extensive relationship at least in the region of the ankle, lower leg, and mid-foot;

an inner ankle brace installed between the inner and outer side walls of the outer brace, said inner brace having medial and lateral side walls for disposition in generally covering relationship to the medial and lateral sides of the ankle, said inner brace having a top edge that wraps around the lower leg, said top edge having ends that come toward one another forming a leg opening disposed beneath the leg opening of the outer brace, a bottom edge that wraps around the mid-foot area, said bottom edge having ends that come toward one another to form a foot opening located rearwardly of the foot opening of the outer brace, and first and second forward edges extended between the top and bottom edges, said first and second forward edges having forwardly extended arms, said side walls of the outer brace having arm openings proximate the outer brace forward edges for extension of the ends of said arms of the inner brace on the medial and lateral sides, the ends of said arms on the inner brace extended through the arm openings of the outer brace, and means for fastening the ends of the arms with respect to one another to place the inner brace in tension around the lower leg, ankle and foot independently of the outer brace.

2. The ankle restraint device of claim 1 including: a rear vertical seam connecting the inner brace and the outer brace at the rear of the foot, and a lower horizontal seam connecting the inner brace and the outer brace beneath the sole of the foot.

3. The ankle restraint device of claim 2 wherein: said outer brace has a lower rearward edge defining a heel opening, said inner brace having a rear strap connected to the lateral and medial side walls extending rearwardly from the upper portion of the side walls positioned aproximately at the upper extremity of the heel, said rear strap extending around the rear of the lower leg above the upper heel extremity, and a bottom strap extended from the lower portions of the side walls and spaced from the rear strap by a heel opening, said bottom strap extending beneath the foot around the lower extremity of the heel.

4. The ankle restraint device of claim 3 wherein: said forward edges of the outer brace have an aligned array of lace eyelets, said outer brace having upper and lower arm openings adjacent the forward edges on the lateral and medial sides, said inner brace forward edges having upper and lower arms on the lateral and medial sides thereof extending through corresponding upper and lower arm openings of the outer brace, said ends of said arms having lace eyelets, and said means for connecting the forward edges of the inner and outer braces being comprised as a lace, said eyelets of the inner and outer brace being positioned so as to be in general alignment for receipt of said lace for fastening the edges together.

5. The ankle restraint device of claim 4 including: a plurality of stiffening members located on and fastened to the lateral and medial sides of the inner brace, said stiffening members on each side of the inner brace including a first set of stiffening members extending from a location proximate the sole of the foot to a location proximate the upper edge of the inner brace generally passing over the malleous, and a second set of stiffening members extending from proxiamate the arch of the foot to the forward edge of the inner brace at the front superior foot surface.

6. The ankle restraint device of claim 5 wherein: said inner brace includes first and second plies of flexible sheet-like material, said stiffening members being embedded between the first and second plies by a plurality of zig-zag stitching seams, each said stiffening member being comprised of a wire element formed of a plurality of interwoven wire strands.

7. The ankle restraint device of claim 6 including: a tongue having a portion hingedly fixed proximate the lower end of one of the forward edges of the outer brace and moveable to a position in covering relationship to the front superior foot surface.

8. The ankle restraint device of claim 4 including: an item of outer footwear apparel having a sole, side walls, an upper edge, said upper edge having ends configured to extend around the lower leg toward one another forming a leg opening, a toe portion, and first and second forward edges extending from the toe portion to the ends of the upper edge, said forward edges having a second array of lace eyelets, a second lace trained through the second lace eyelets for fastening the first and second forward edges of the item of foot apparel with respect to one another, said inner and outer ankle braces being installed in said item of outer footwear apparel with the forward edges of the inner and outer braces adjacent the first and second forward edges of the item of outer footwear apparel, and means connecting a lower portion of the outer side wall of the outer brace to inner portions of the item of footwear apparel.

9. The ankle restraint device in claim 8 including: a sole cushion installed inside the item of outwear foot apparel.

10. An ankle restraint device comprising:
a first brace formed of a flexible sheet-like member having a shape to conform to the lower leg, ankle region and mid-foot of the wearer, having a closable upper edge for defining a leg opening, and closable first and second forward edges adapted to extend toward one another around the front superior foot surface, means for fastening the forward edges to place the first brace in tension around the lower leg, ankle region and mid-foot, said first brace formed of inner and outer layers of flexible sheet-like material peripherally fastened together along said upper edge and forward edges;
a second brace installed between the inner and outer layers of the first brace and having a shape to conform to the lower leg, ankle region and mid-foot including an upper strap that extends around the back of the foot at the upper heel extremity, and a lower strap that extends beneath the sole of the foot proximate the lower heel extremity, said second brace formed of a sheet-like member having first and second edges that come toward one another in order to place the second brace in tension around the ankle region, said first and second edges having arm portions for fastening together to hold the second brace in tension in order to bind the heel;
said first brace having arm openings proximate the forward edges thereof for extension of the arm portions of the second brace exteriorly of the first brace for fastening together, said arm portions of the second brace extended through the openings of the first brace, and means for fastening together the arm portions on the first and second edges of the second brace.

11. The ankle restraint device of claim 10 wherein: the arm portions on the first edge of the second brace and the arm portions on the second edge of the second brace each have lace eyelets, and means connecting the arm portions comprising a lace.

12. The ankle restraint device of claim 11 wherein: said first brace has forward edges that come together over the front of the foot; said edges on the second brace being comprised as forward edges, said arm portions on the forward edges of the second brace being in alignment with the first and second forward edges of the first brace, said first and second forward edges of the first brace having lace eyelets, and means fastening the first and second edges of the first brace comprised as said lace fastening the arm portions of the second brace.

13. An ankle restraint device comprising:
a first brace formed of a flexible sheet-like member having a shape to conform to the lower leg, ankle region and mid-foot of the wearer, having a closable upper edge for defining a leg opening and closable first and second forward edges, said first brace formed of inner and outer layers of flexible sheet-like material peripherally fastened together;
a second brace disposed between the inner and outer layers of the first brace and having a shape to conform to the lower leg, ankle region and mid-foot, said second brace formed of a sheet-like member with first and second edges that come toward one another in order to place the second brace in tension around the ankle region, said first and second edges having arm portions for fastening together to hold the second brace in tension;
said first brace having arm openings proximate the forward edges thereof for extension of the arm portions of the second brace exteriorly of the first brace for fastening together, said arm portions of the second brace extended through the openings of the first brace, and means for fastening together the arm portions on the first and second edges of the second brace;
said second brace having an upper strap that extends around the back of the foot at the upper heel extremity, and a lower strap that extends beneath the sole of the foot proximate the lower heel extremity in order to bind the heel upon tensioning of the arm portions on the first and second edges;

said second brace having lateral and medial sides, each side having first and second sets of stiffening members, said first set of stiffening members extending from the vicinity of the sole up along the side to the upper edge covering the malleolus, said second set of stiffening members extending from the vicinity of the sole up across the front superior foot surface.

14. The ankle restraint devise of claim 13 wherein: said second brace is comprised of first and second plies of flexible sheet-like material, said stiffening members being embedded between said plies, and stitching around and over the stiffening stay members to hold the stay members in place.

15. The ankle restraint device of claim 14 wherein: said stiffening members are comprised of a plurality of inter-woven wire strands.

16. The ankle restraint device of claim 15 wherein: said forward edges of the first brace have a plurality of lace eyelets, said arm portions of the second brace having lace eyelets in alignment with the lace eyelets of the forward edges of the first brace, and a common lace threaded through the eyelets of the forward edges of the first brace and the arm portions of the second brace.

17. The ankle restraint device of claim 11 including: an item of outer footwear apparel having a sole, side walls, an upper edge, said upper edge having ends configured to extend around the lower leg toward one another forming a leg opening, a toe portion, and first and second forward edges extending from the toe portion to the ends of the upper edge, said forward edges having a second array of lace eyelets, a second lace trained through the second lace eyelets for fastening the first and second forward edges of the item of foot apparel with respect to one another, said first and second braces being installed in said item of outer footwear apparel with the forward edges of the first brace and second brace adjacent the first and second forward edges of the item of footwear apparel, and means connecting the lower portion of the side walls of the first brace to inner portions of the item of footwear apparel.

18. The ankle restraint device of claim 13 including: an item of outer footwear apparel having a sole, side walls, an upper edge, said upper edge having ends configured to extend around the lower leg toward one another forming a leg opening, a toe portion, and first and second forward edges extending from the toe portion to the ends of the upper edge, said forward edges having a second array of lace eyelets, a second lace trained through the second lace eyelets for fastening the first and second forward edges of the item of foot apparel with respect to one another, said first and second braces being installed in said item of outer footwear apparel with the forward edges of the first brace and second brace adjacent the first and second forward edges of the item of footwear apparel, and means connecting the lower portion of the side walls of the first brace to inner portions of the item of footwear apparel.

* * * * *

UNITED STATES PATENT AND TRADEMARK OFFICE
CERTIFICATE OF CORRECTION

PATENT NO. : 4,960,135

DATED : October 2, 1990

INVENTOR(S) : RONALD E. NELSON

It is certified that error appears in the above-identified patent and that said Letters Patent is hereby corrected as shown below:

Abstract, line 7, "remainer" should be -- remainder --.

Col. 2, line 34, following "there" insert -- is --.

Col. 2, line 47, "undo" should be -- undue --.

Col. 2, line 53, "undo" should be -- undue --.

Col. 2, line 63, "undo" should be -- undue --.

Col. 3, line 24, "canvass" should be -- canvas --.

Col. 3, line 65, "malleous" should be -- malleolus --.

Col. 4, line 26, "external" should be -- extend --.

Col. 4, line 47, "malleous" should be -- malleolus --.

Col. 6, line 65, "aproximately" should be -- approximately --.

Col. 7, line 25, "proxiamate" should be -- proximate --.

Col. 7, line 58, "outwear foot" should be -- outer footwear --.

UNITED STATES PATENT AND TRADEMARK OFFICE
CERTIFICATE OF CORRECTION

PATENT NO. : 4,960135
DATED : October 2, 1990
INVENTOR(S) : Ronald E. Nelson

It is certified that error appears in the above-identified patent and that said Letters Patent is hereby corrected as shown below:

Column 8, line 32, delete from "said" of line 1 of claim 12 to "foot" on line 3.

Signed and Sealed this

Twenty-ninth Day of September, 1992

Attest:

DOUGLAS B. COMER

Attesting Officer    Acting Commissioner of Patents and Trademarks